United States Patent [19]

Floyd et al.

[11] Patent Number: 5,932,695
[45] Date of Patent: *Aug. 3, 1999

[54] SYNTHESIS OF HYDROXAMIC ACID DERIVATIVES

[75] Inventors: Christopher David Floyd; Christopher Norman Lewis, both of Oxford, United Kingdom

[73] Assignee: British Biotech Pharmaceuticals Ltd., Oxford, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,499

[22] PCT Filed: Feb. 26, 1996

[86] PCT No.: PCT/GB96/00428

§ 371 Date: Mar. 24, 1997

§ 102(e) Date: Mar. 24, 1997

[87] PCT Pub. No.: WO96/26223

PCT Pub. Date: Aug. 29, 1996

[30] Foreign Application Priority Data

Feb. 24, 1995 [GB] United Kingdom ............... 9503749

[51] Int. Cl.$^6$ .............. C07K 1/04; C08G 63/48
[52] U.S. Cl. ............ 530/333; 530/331; 530/334; 525/54.11; 525/374; 525/377
[58] Field of Search .................... 530/331, 333, 530/334; 525/54.11, 374, 377

[56] References Cited

U.S. PATENT DOCUMENTS 4,461,876  7/1984  Lieberman ............... 525/374
4,868,248  9/1989  Sparapany ............... 525/380

FOREIGN PATENT DOCUMENTS 0216499  4/1987  European Pat. Off. .
0514648  11/1992  European Pat. Off. .
0561722  9/1993  European Pat. Off. .

OTHER PUBLICATIONS

International Search Report for PCT/GB96/00428.

PCT Written Opinion for PCT/GB96/00428.

Letter by Applicant in reply to PCT written opinion for PCT/GB96/00428.

PCT International Preliminary Examination Report for PCT/GB96/00428.

(1) Chemical Abstracts, vol. 77, No. 24, Dec. 11, 1972, Abstract No. 153114e, Chernyshev, V.P.: "Maleic Anhydride Copolymer", p. 39, col. 2 & SU,A,342 865 (Institute of Fine Chemical Technology, Moscow) Jun. 22, 1972.

(2) Polymer Bulletin, vol. 32, No. 3, 1994, pp. 273–279, XP002003868, Taek Seung Lee: "Synthesis of Porous Poly-(Hydroxamic Acid) from Poly(Ethyl Acrylate–Co–Divinylbenzene)".

*Primary Examiner*—Bennett Celsa
*Attorney, Agent, or Firm*—Hale and Dorr LLP

[57] ABSTRACT

This invention is direct to a solid phase reaction product of a solid substrate carrying a plurality of covalently bound hydroxylamine or protected hydroxylamine groups. The solid solid phase reaction product may be used for the synthesis of hydroxamic acid derivatives or a combinatorial library of such compounds.

12 Claims, No Drawings

SYNTHESIS OF HYDROXAMIC ACID DERIVATIVES

This application is a §371 of PCT/6896/00428, filed on Feb. 26, 1996.

The present invention relates to a solid phase reaction component, and to a process for the use of such a component in the synthesis of individual hydroxamic acid derivatives or a combinatorial library of such compounds. In particular, the solid phase reaction component may be used for the synthesis of hydroxamic acids that are inhibitors of zinc metalloproteinase enzymes. Such enzymes are involved in tissue degradation and the release of tumour necrosis factor from cells.

BACKGROUND OF THE INVENTION

Solid Phase Synthesis

Solid phase synthesis is an established and effective method for the preparation of peptides, and offers advantages over conventional solution phase chemistry in terms of purification and simplicity (Atherton E, Sheppard R C, Solid Phase Peptide Synthesis: A Practical Approach; IRL Press at Oxford University Press: Oxford, 1989). Solid phase synthesis may also be used for the preparation of non-peptide molecules (Leznoff C C, Acc. Chem. Res., 1978, 11, 327–333) and recently there has been considerable interest in the application of this methodology to the synthesis of combinatorial libraries for biologically active lead compound optimisation and discovery (Moos W H et al., Annu. Rep. Med. Chem., 1993, 28, 315–324).

Solid phase synthesis requires an appropriate solid substrate which carries a plurality of functional groups to which the first reactive entity in the proposed synthesis may be covalently coupled, and from which the desired molecule may be cleaved after assembly. The solid substrate should be compatible with the solvents and reaction conditions that are to be used in the peptide or non-peptide synthesis.

The final step in solid phase synthesis is the cleavage of the covalent bond between the desired peptide or non-peptide molecule and the linker. It is desirable that the conditions for the cleavage are orthogonal to those used during the reactions employed for the synthesis of the peptide or non-peptide on the solid support such that inadvertent cleavage does not occur during the synthesis. Furthermore, the conditions for cleavage should be relatively mild such that they do not result in degradation of the desired peptide or non-peptide. Solid substrates which present hydroxyl groups as the points of attachment for the first stage of the synthesis are commonly used, for example substrates which present hydroxyl groups as derivatives of benzyl alcohol, the peptide or non-peptide being attached as a benzyl ester and cleaved by hydrolysis, transesterification or aminolysis to release the peptide or non-peptide as a carboxylic acid, carboxylate ester or as a carboxamide. Also used are substrates which present amino groups, for example as derivatives of diphenylmethylamine, the peptide or non-peptide being attached as a carboxamide and cleaved by hydrolysis to release the peptide or non-peptide as a carboxamide. Substitution of such linkers by a nitro group can enable the photolytic cleavage of the peptides or non-peptides from the residue of the solid substrate.

Hydroxamic Acid Derivatives

Certain hydroxamic acid derivatives possess useful biological activities. Examples of such hydroxamic acids include compounds that inhibit urease (Odake S et al., Chem. Pharm. Bull., 1992, 40, 2764–2768), trypanosome glycerol-3-phosphate oxidase (Grady et al., Mol. Biochem. Parasitol., 1986, 19, 231–240), dehydropeptidase-1 (EP-B-276,947), ribonucleotide reductase (Farr R A et al., J. Med. Chem., 1989, 32, 1879–1885), 5-lipoxygenase (Kerdesky F A J et al., Tetrahedron Lett., 1985, 26, 2134–2146; U.S. Pat. No. 4,731,382), substance P degradation (Laufer R et al., Eur. J. Biochem., 1985, 150, 135–140), cardiovascular metalloproteinase enzymes (Turbanti L et al., J. Med. Chem., 1993, 36, 699–707; WO-9428012) and matrix metalloproteinase enzymes (Schwartz M A. Van Wart H E, Prog. Med. Chem., 1992, 29, 271–334).

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal, epidermal or gastric ulceration, and tumour metastasis, invasion and growth. It has been found that hydroxamic acid MMP inhibitors can also inhibit the production of the cytokine tumour necrosis factor (herein referred to as "TNF") (Mohler et al., Nature, 1994, 370, 218–220; Gearing A J H et al., Nature 1994, 370, 555–557; McGeehan G M et al., Nature 1994, 370, 558–561). Compounds which inhibit the production or action of TNF are thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury. Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Classes of MMP Inhibitors

The known hydroxamic acid MMP inhibitors may be grouped into three classes; i) peptidyl hydroxamates, ii) succinyl hydroxamates and iii) arylsulfonamido hydroxamates.

i) The following patent publication discloses peptidyl hydroxamic acid-based MMP inhibitors:

EP-A-345359 (Fuji)

The tri- and tetra-peptidyl hydroxamic acid derivatives disclosed in the above publication and described elsewhere (Odake S et al., Chem. Pharm. Bull., 1990, 38, 1007–1011; Odake S et al., Chem. Pharm. Bull., 1991, 39, 1489–1494; Odake S et al., Biochem. Biophys. Res. Commun., 1994, 199, 1442–1446) can be regarded as having the following basic structure (I):

$$R_1-X_1-X_2-X_3-NHOH \qquad (I)$$

wherein the four groups $R_1$, $X_1$, $X_2$ and $X_3$ may vary according to the detailed disclosure of each of the publications.

ii) The following patent publications disclose succinyl hydroxamic acid-based MMP inhibitors:

U.S. Pat. No. 4,599,361 (Searle)
EP-A-0236872 (Roche)
EP-A-0274453 (Bellon)
WO 90/05716 (British Bio-technology)
WO 90/05719 (British Bio-technology)
WO 91/02716 (British Bio-technology)
EP-A-0489577 (Celltech)
EP-A-0489579 (Celltech)
EP-A-0497192 (Roche)
WO 92/13831 (British Bio-technology)
WO 92/22523 (Research Corporation Technologies)
WO 93/09090 (Yamanouchi)
WO 93/09097 (Sankyo)
WO 93/20047 (British Bio-technology)
WO 93/24449 (Celltech)
WO 93/24475 (Celltech)
U.S. Pat. No. 5,256,657 (Sterling Winthrop)
EP-A-0574758 (Roche)
WO 94/02446 (British Bio-technology)
WO 94/02447 (British Bio-technology)
WO 94/21612 (Otsuka)
WO 94/25434 (Celltech)
WO 94/25435 (Celltech)

The hydroxamic acid derivatives disclosed in the above publications can be regarded as having the following basic structure (II):

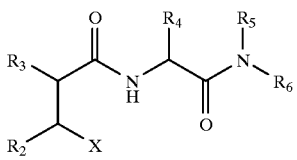

(II)

wherein the five substituents $R_2$–$R_6$ may vary according to the detailed disclosure of each publication. The balance of intrinsic level of activity, degree of specificity of inhibition of particular categories of MMP, physicochemical and pharmacokinetic properties can vary in an unpredictable way as the substituents $R_2$–$R_6$ are varied.

iii) The following patent publication discloses arylsulfonamido hydroxamic acid-based MMP inhibitors:

EP-A-606046 (Ciba-Geigy)

The hydroxamic acid derivatives disclosed in the above publication can be regarded as having the following basic structure (III):

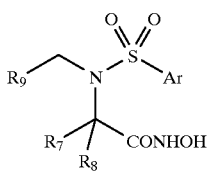

(III)

wherein the four substituents $R_7$–$R_9$ and Ar may vary according to the detailed disclosure of the publication.

BRIEF DESCRIPTION OF THE INVENTION

A key step in the synthesis of many hydroxamic acid derivatives is the reaction of a carboxylic acid group with hydroxylamine or a protected hydroxylamine by first activating the carboxylic acid or by conducting the reaction in the presence of an activating agent. In a recent patent application the possibility that peptidyl hydroxamic acids might be prepared using solid phase synthesis was recognised (WO 94/28012). However, the proposed protocol involved first synthesis of the peptide on a solid support followed by cleavage from the support and subsequent conversion of the C-terminal carboxylic acid group to a hydroxamic acid by a method analogous to that indicated above.

It was the hypothesis of the present inventors that hydroxamic acid derivatives might be prepared by the reaction of a solid substrate presenting hydroxylamine groups as the point of attachment for the first reactive entity of the synthesis, then reacting the resultant solid phase intermediate with the further reactive entities required for the desired synthesis, followed by a cleavage step to release the final hydroxamic acid derivative. Such a hydroxylamine-presenting solid phase reaction component could simplify the synthesis and purification of biologically active hydroxamic acid derivatives, for example MMP inhibitors of the three classes referred to above, and could be applicable to the automation of such syntheses. In addition it would enable the solid phase synthesis of combinatorial libraries of hydroxamic acids. Thus, this invention makes available such hydroxylamine-presenting solid phase reaction components, and provides a process for their use in solid phase synthesis of hydroxamic acid derivatives.

DETAILED DESCRIPTION OF THE INVENTION

The present invention provides, in one of its aspects, a solid phase reaction component comprising a solid substrate, substantially insoluble in aqueous or organic reaction media, carrying a plurality of covalently bound hydroxylamine or protected hydroxylamine groups of formula (A) or (B)

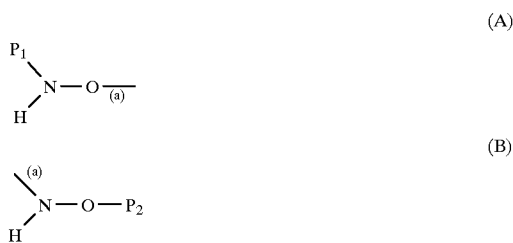

wherein $P_1$ is hydrogen or an amino protecting group and $P_2$ is hydrogen or a hydroxyl protecting group, and the bond designated (a) is one which covalently links the group (A) or (B) to the residue of the solid substrate and is cleavable under acid conditions or by photolysis.

The bond designated (a) covalently links the group (A) or (B) to the residue of the solid substrate. The residue of the solid substrate will usually comprise a be substrate carrying suitable linker groups which indirectly link the hydroxylamine group (A) or (B) to the base substrate. Suitable base substrates include those known in the art of solid phase peptide synthesis (see for example those described in Stewart J M and Young J D, Solid Phase Peptide Synthesis, 2nd Ed; Pierce Chemical Company: Rockford, Ill., 1984). They include inorganic substrates, for example kieselguhr, silica gel and controlled pore glass, and polymeric organic substrates, for example polystyrene, polypropylene, polyethylene glycol, polyacrylamide, cellulose, as well as composite inorganic/polymeric substrates such as polyacrylamide supported within a matrix of kieselguhr particles. Such known base substrates include amino and hydroxy functionalised solid substrates, ie those which are chemically modified by introduction of amino or hydroxyl groups, to serve as convenient points for further chemical manipulation. Examples of particular amino or hydroxy functionalised base substrates are: hydroxymethyl copoly(styrene-1 or 2% divinylbenzene), which can be represented as

wherein P represents the polymer backbone;

benzhydrylamine copoly(styrene-1 or 2% divinylbenzene) ("BHA Resin") or methyl benzhydrylamine copoly(styrene-1 or 2% divinylbenzene) ("MBHA Resin"), which can be represented as

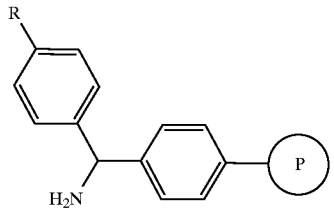

wherein P represents the polymer backbone and R is hydrogen or methyl respectively;

polyethylene glycol polystyrene ("PEG-PS");

poly(dimethylacrylamide)polystyrene composite ("Polyhipe");

polyacrylamide Kieselguhr composite ("Macrosorb");

or functionalised controlled pore glass.

Thus, in the case of peptide synthesis, hydroxyl- or amino-carrying linker groups can be introduced onto such amino and hydroxy functionalised base substrates. In case of a hydroxyl-carrying linker group, the first amino acid of the peptide to be constructed may be attached as an ester formed between the linker-presented hydroxyl group and the carboxyl group of the amino acid. In the case of amino-carrying linker groups, the first amino acid of the peptide to be constructed may be attached as a carboxamide formed between the linker-presented amino group and the carboxyl group of the amino acid.

In an analogous fashion, the solid phase reaction components of the present invention may comprise a base substrate, for example of the kind referred to above, and a linker group which presents the hydroxylamine group (A) or (B) for reaction with the first reactive entity in the proposed synthesis. A preferred embodiment of this aspect of the invention is a solid phase reaction component, comprising a solid substrate, substantially insoluble in aqueous or organic reaction media, carrying a plurality of groups of formula (IV):

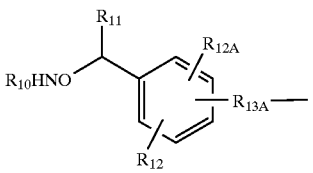

wherein
R$_{10}$ represents hydrogen or (phenyl)CH$_2$—, optionally substituted in the phenyl ring by one or more substituents selected from C$_1$–C$_6$ alkyl, C$_1$–C$_6$ alkoxy, halogen, nitrile or NO$_2$;

R$_{11}$ represents hydrogen, C$_1$–C$_6$ alkyl, or phenyl optionally substituted by one or more substituents selected from C$_1$–C$_6$ alkyl, C$_1$–C$_6$ alkoxy, halogen, nitrile or NO$_2$;

R$_{12}$ and R$_{12A}$ independently represent hydrogen, C$_1$–C$_6$ alkyl, C$_1$–C$_6$ alkoxy, halogen, nitrile or NO$_2$;

R$_{13}$ represents a group —(X$^1$)$_q$—Y— wherein q is 0 or 1, X$^1$ represents —C(=O)—, —CH$_2$—, —CH$_2$C(=O)—, —O(CH$_2$)$_n$C(=O)—, —O(CH$_2$)$_n$C(=O)—(A$^1$)$_m$—, or —O(CH$_2$)$_n$C(=O)—(A$^1$)$_m$—B$^1$—, wherein n is an integer from 1 to 6, m is 0 or 1, A$^1$ represents —O—CH(R$^1$)—NH— wherein R$^1$ is the side chain of a natural or unnatural alpha amino acid, B$^1$ represents a spacer group —NH(CH$_2$)$_p$— wherein p is 0 or an integer from 1 to 6, and Y represents —O— or —NH—.

In this embodiment, the group (IV) is linked to the solid substrate via "Y", defined as —O— or —NH—. It will be apparent that these "Y" groups may be incorporated during synthesis of the solid phase reaction component of the invention, by starting with an amino or hydroxy functionalised base substrate, for example hydroxymethylpolystyrene, hydroxymethyl copoly(styrene-1% divinylbenzene), benzhydrylaminepolystyrene, benzhydrylamine copoly(styrene-1% divinylbenzene ("BHA Resin"), methyl benzhydrylaminepolystyrene, methyl benzhydrylamine copoly(styrene-1% divinylbenzene, ("MBHA Resin"); polyethylene glycol polystyrene ("PEG-PS"); poly (dimethylacrylamide)polystyrene composite ("Polyhipe"); polyacrylamide Kieselguhr composite ("Macrosorb"); or functionalised controlled pore glass.

Another preferred embodiment of this aspect of the invention is a solid phase reaction component, comprising a solid substrate, substantially insoluble in aqueous or organic reaction media, carrying a plurality of groups of formula (IVA):

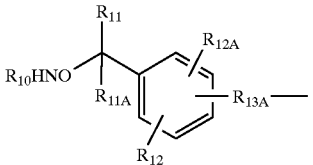

wherein R$_{10}$ R$_{11}$ R$_{12}$ and R$_{12A}$ are as defined in formula (IV), R$_{11A}$ is as defined for R$_{11}$ in formula (IV), and R$_{13A}$ is a bond or is as defined for R$_{13}$ in formula (IV).

As used herein the term "C$_1$–C$_6$ alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl. "$C_1$–$C_6$ alkoxy" means an alkoxy group wherein the alkyl part is $C_1$–$C_6$ alkyl.

In the preferred solid phase reaction component of the invention carrying a plurality of groups of formula (IV), referred to above:

$R_{10}$ may for example be hydrogen, 4-methoxybenzyl or 2,4-dimethoxybenzyl. Presently preferred are compounds in which $R_{10}$ is hydrogen.

$R_{11}$ may for example be hydrogen, methyl, phenyl, 4-methylphenyl, 4-methoxyphenyl or 2,4-dimethoxyphenyl. Presently preferred are compounds in which $R_{11}$ is hydrogen.

$R_{12}$ may for example be hydrogen or methoxy. Presently preferred are compounds in which $R_{12}$ is hydrogen.

$R_{13}$ together with the base substrate to which it is attached may for example be oxymethyl-copoly(styrene-1 divinylbenzene)resin, oxymethyl-copoly (styrene-2% divinylbenzene)resin, oxyacetomidomethylpolyethyleneglycol-copoly (styrene-1% divinylbenzene)resin or oxyacetomidomethylpolyethyleneglycol-copoly (styrene-2% divinylbenzene)resin. Presently preferred are compounds in which $R_{13}$ together with the base substrate to which it is attached is oxymethyl-copoly (styrene-1% divinylbenzene)resin.

Specific preferred solid phase reaction components of the invention carrying a plurality of groups of formula (IV), are:

4-(O-Methylhydroxylamine)phenoxymethyl-copoly (styrene-1% divinylbenzene)-resin (100–200 mesh), 4-[4-(O-Methylhydroxylamine)-3-methoxyphenoxy]-(N4-methylbenzhydryl)butyramide-copoly(styrene-1%-divinylbenzene)-resin (100–200 mesh), 4-(2',4'-Dimethoxyphenyl-O-methylhydroxylamine)-phenoxymethyl-copoly(styrene-1%-divinylbenzene)-resin (100–200 mesh), and 4-[4-(1-Aminooxyethyl)-2-methoxy-5-nitrophenoxy]-(N4-methylbenzhydryl)butyramide-copoly(styrene-1%-divinylbenzene)-resin (100–200 mesh).

A specific preferred solid phase reaction component of the invention carrying a plurality of groups of formula (IVA), is: O-Hydroxylamine-2'-chlorotrityl-copoly(styrene-1%-divinylbenzene)-resin (200–400 mesh).

Solid phase reaction components of the invention may be prepared by standard synthetic techniques from solid substrates which are in general commercially available or readily derivable from commercially available materials. For example, the preferred solid phase reaction component of the invention carrying a plurality of groups of formula (IV), referred to above may be prepared by treating a solid substrate, substantially insoluble in aqueous or organic reaction media, carrying a plurality of benzyl alcohol groups of general formula (V)

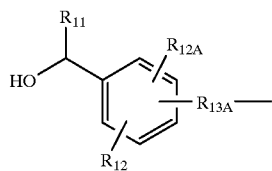

(V)

wherein $R_{11}$–$R_{13}$ are as defined for general formula (IV) with a compound of formula (VI)

$$R_{10}NHOH \quad (VI)$$

wherein $R_{10}$ is as defined for general formula (IV) but is other than hydrogen under Mitsunobu reaction conditions using triphenylphosphine and diethylazo-dicarboxylate or similar reagents. The preferred solid phase reaction component of the invention carrying a plurality of groups of formula (IV), referred to above, wherein $R_{10}$ is hydrogen may be prepared by treating a solid substrate, substantially insoluble in aqueous or organic reaction media, carrying a plurality of groups of general formula (VII)

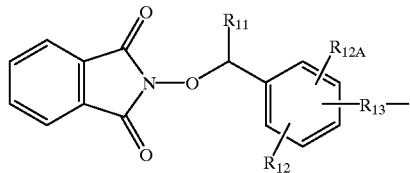

(VII)

wherein $R_{11}$–$R_{13}$ are as defined for general formula (IV) with hydrazine.

A solid substrate, substantially insoluble in aqueous or organic reaction media, carrying a plurality of groups of general formula (VII) can be prepared by coupling a phthalimide derivative of formula (VIII) with a solid substrate, substantially insoluble in aqueous or organic reaction media, carrying a plurality of benzyl alcohol groups of general formula (V) defined above

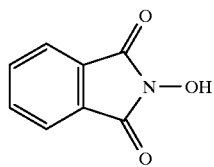

(VIII)

wherein $R_{11}$–$R_{13}$ are as defined in general formula (IV) under Mitsunobu reaction conditions using triphenylphosphine and diethyl azodicarboxylate or similar reagents. Solid substrates, substantially insoluble in aqueous or organic reaction media, carrying a plurality of groups of general formula (V), and compounds of formulae (VI) and (VIII), are known in the art or may be prepared by procedures known to those skilled in the art.

In an analogous manner, the preferred solid phase reaction components of formula (IVA) above may be prepared. Alternatively, the hydroxylamine group may be introduced by displacement of a leaving group present in the base substrate, eg a halogen group such as chloro, using a suitably protected hydroxylamine derivative, eg a compound of formula (Viii) above.

The choice of solvent for syntheses based on a solid phase reaction component of the invention will of course depend on the nature of the reagents to be reacted with such component, but will also be influenced by the nature of that component. For example many of the polymer reaction components of the invention may swell to a greater or lesser extent in certain solvents, and generally such swelling will be desirable for the efficiency of the reaction with other reagents in the desired synthesis.

Solid phase reaction components of the invention presenting groups of type (B) above will generally be accessable (i) by displacement of a leaving group (eg a triflate, mesylate or halogen group) from the desired base substrate carrying such leaving groups, using hydroxylamine or O-protected hydroxylamine, or (ii) by reacting the desired base substrate carrying carbonyl groups with hydroxylamine or O-protected hydroxylamine to form oxime groups, and then reducing the oxime double bond, eg using a metal hydride.

In another of its aspects, the present invention comprises a process for the preparation of a desired synthetic product whose structure is characterised by the presence of a covalently bonded hydroxamic acid group —CONHOH, which process comprises the steps of:

(i) forming a mixture of a liquid reaction medium and a solid phase reaction component which is substantially insoluble in the said liquid reaction medium and carries a plurality of covalently bound moieties of formula (A1) or (B1)

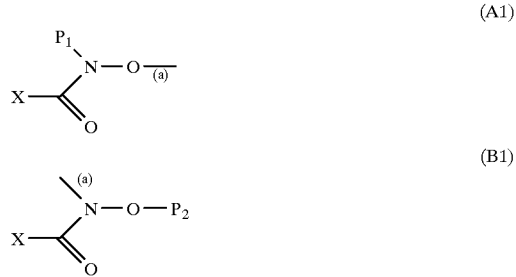

in which formulae X represents the residual, non-hydroxamate, partial structure of the desired product, $P_1$ represents hydrogen or an amino-protecting group, P2 represents hydrogen or a hydroxyl protecting group, and the bond designated (a) is one which covalently links the moieties (A1) or (B1) to the residue of the solid substrate and is cleavable under acid conditions or by photolysis; and (ii) in the resultant mixture, cleaving the said bond designated (a) and, if $P_1$ or $P_2$ as the case may be is not hydrogen, removing that protecting group $P_1$ or P2 before, after or during cleavage of bond (a); and (iii) separating the resultant liquid reaction phase from the resultant reaction solids and recovering the desired product from the separated liquid reaction phase.

Trifluoroacetic acid will generally be suitable for the acid hydrolysis of the bond (a). Depending on the structure of the linker group, solutions of trifluoroacetic acid ranging from 95% v/v to 1% v/v may be used. In Example 5 below, the linker group is photolytically cleavable, and in the remaining Examples it is cleavable by acid hydrolysis.

In step (i) of the above process the solid phase reaction component which carries a plurality of moieties of formula (A1) or (B1) may be derived by appropriate chemical modification from the solid phase reaction component of the invention, described above, carrying a plurality of hydroxylamine or protected hydroxylamine groups of formula (A) or (B).

In the process of the invention, the solid phase reaction component may be in the form of a finely divided solid, or a web, membrane or open pore matrix. For example, the liquid reaction medium may be mixed with the solid phase reaction product by passing the former through a liquid permeable bed or column of the latter, or by contacting the former with a discrete quantity of the latter in finely divided form in a reaction vessel.

The solid phase reaction component and process of the present invention are applicable in syntheses of the following general types, Schemes 1 and 2;

Scheme 1

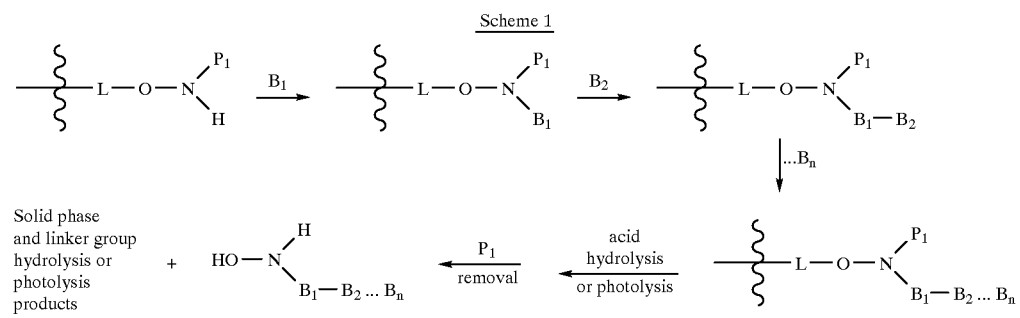

Scheme 2

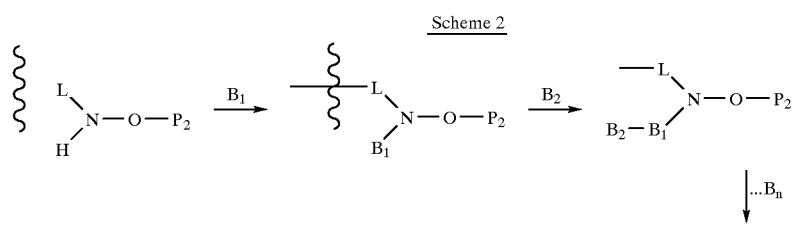

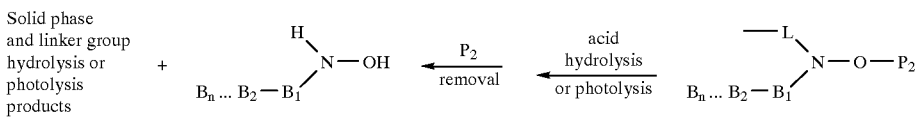

In schemes 1 and 2, the vertical wavy line represents the base solid substrate, L represents a linker group, $P_1$ and $P_2$ are as defined above, and $B_1 \ldots B_n$ are the reaction building blocks for the synthesis of the desired product. In both cases, the desired product is released from the solid phase support by acid hydrolysis or photolysis of the bond designated (a) in formula (A) or (B), and the protecting group $P_1$ or P2 may be removed in the same or a separate step depending on its identity.

If desired, the intermediate solid phase reaction product can by isolated and physically partitioned into a plurality of portions after the addition of each building block $B_1 \ldots B_n$. Each resultant portion may then be reacted with a different next building block. This process facilitates the parallel synthesis of a multiplicity of different hydroxamate end products.

Alternatively, the solid phase reaction component can be physically partitioned into a plurality of portions and each resultant portion may then be reacted with a different first building block $B_1$. The separate portions may then be mixed to form a single portion which is then split into a plurality of portions. Each resultant portion may then be reacted with a different second building block. The separate portions may then be mixed to form a single portion which is then split into a plurality of portions for the coupling of the different second building blocks $B_2$. This process may be repeated a number of times until the final building block $B_n$ has been added. This process facilitates the combinatorial synthesis of a mixture of a multiplicity of different hydroxamate end products.

Specific applications of the process of the invention are the preparation of hydroxamic acids of the three classes referred to above, namely peptidyl, succinyl and arylsulphonamido hydroxamates.

For the synthesis of peptidyl hydroxamates (formula (I) above) by, for example, Scheme 1, the building blocks $B_1 \ldots B_n$ represent the amino acids for sequential coupling. The first amino acid is coupled to the groups A carried by solid phase reaction component of the invention, for example one of the preferred solid phase reaction components of the invention carrying a plurality of groups of formula (IV) or (IVA). In the latter case, the amino group of the amino acid component may be protected as a 9-fluorenylmethoxycarbonyl ("Fmoc") derivative and the coupling of the amino acid carboxyl group to the nitrogen of the group A carried by the solid phase reaction component of the invention may be facilitated by the use of a coupling agent such as is commonly used in peptide synthesis, for example a carbodiimide (e.g. diisopropylcarbodiimide), a phosphonium salt (e.g. benzotriazol-1-yl-oxy-tris-(dimethylamino)phosphonium hexafluorophosphate) or a uronium salt (e.g. 2-(1H-benzotriazol-1-yl)-1,1,3,3-tetramethyluronium hexafluorophosphate), with the optional addition of an additive such as 1-hydroxybenzotriazole. Alternatively, the coupling reaction may be conducted by preforming an active ester derivative (e.g. pentafluorophenyl ester) of the carboxylic acid component and optionally conducting the reaction in the presence of an additive such as 1-hydroxybenzotriazole. The Fmoc amino protecting group may then be removed by treatment of the reaction product with a basic amine such as piperidine. During the coupling reaction any groups in the amino acid which are potentially reactive under the coupling conditions may be protected from such reaction as is usual in peptide synthesis. Addition of the second and any subsequent amino acids proceeds in a similar manner until the desired peptidyl hydroxamate is finally cleaved from the solid substrate, eg by acid hydrolysis of the bond designated (a), and any protecting groups present in the molecule may be removed before during or after such cleavage, depending on the nature of the protecting groups in question.

For the synthesis of succinyl hydroxamates (formula (II) above) by, for example, Scheme 1, an appropriate choice of building blocks $B_1 \ldots B_n$ to effect the synthesis is made. The first building block will generally be a carboxylic acid (also containing a site suitable for coupling the next building block) which is coupled to the groups A carried by solid phase reaction component of the invention, for example one of the preferred solid phase reaction components of the invention carrying a plurality of groups of formula (IV) or (IVA). Again the coupling of the carboxyl group of the first building block to the nitrogen of the group A carried by the solid phase reaction component of the invention may be facilitated by the use of a coupling agent such as is commonly used in peptide synthesis, for example a carbodiimide (e.g. diisopropylcarbodiimide), a phosphonium salt (e.g. benzotriazol-1-yl-oxy-tris-(dimethylamino)phosphonium hexafluorophosphate) or a uronium salt (e.g. 2-(1H-benzotriazol-1-yl)-1,1,3,3-tetramethyluronium hexafluorophosphate), with the optional addition of an additive such as 1-hydroxybenzotriazole. Alternatively, an activated ester, for example a pentafluorophenyl ester, of the first carboxylic acid building block may be coupled to the group A carried by the solid phase reaction component of the invention in the presence of dimethylaminopyridine. A particular first carboxylic acid building block may be one of formula (IX)

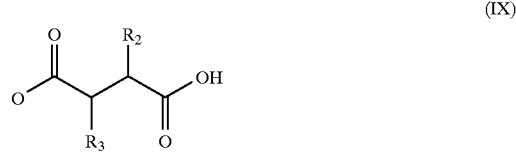

(IX)

wherein $R_2$ and $R_3$ are groups dictated by the desired succinyl hydroxamate final product and $R_{14}$ is a carboxyl protecting group which is compatible with solid phase synthesis such as an allyl group. Where the compound (IX) is coupled to the solid phase reaction components of the invention in this way, the $R_{14}$ carboxyl protecting group in the resultant product may be converted to a carboxylic acid group by deprotection. In the case where $R_{14}$ is an allyl group deprotection may be acheived by palladium catalysis. Suitable reagents for this step are $Pd(PPh_3)_4$ or $Pd(OAc)_2$/triphenylphosphine, and the reaction is usually conducted in the presence of an allyl acceptor such as morpholine. The carboxylic acid group thus generated may then be used as the point of attachment for the second building block, which will generally be an amine of formula (X)

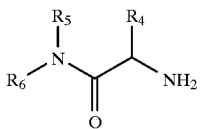

(X)

wherein $R_4$–$R_6$ are again groups dictated by the desired succinyl hydroxamate final product. The methods described above and common in peptide synthesis are used to effect the coupling of the amine group of (X) with the carboxylic acid group of the first building block now carried on the solid phase reaction component. During the coupling reactions of the foregoing assembly process, any groups in the first and second building blocks which are potentially reactive under the coupling conditions may be protected from such reaction as is usual in peptide synthesis. After assembly of the desired succinyl hydroxamate, the product may be cleaved from the solid substrate, eg by acid hydrolysis of the bond designated (a), and any protecting groups present in the molecule may be removed before, during or after such cleavage, depending on the nature of the protecting groups in question.

For the synthesis of arylsulphonamide hydroxamates (formula (III) above) by the method of, for example, Scheme 1, an appropriate choice of building blocks $B_1$ . . . $B_n$ to effect the synthesis is made. The first building block will either be an alpha amino acid in which the alpha amino group is protected (for example as a 9-fluorenylmethoxycarbonyl ("Fmoc") or allyloxycarbonyl ("Aloc") derivative), and the substituents on the alpha C atom (corresponding to $R_7$ and $R_8$ in formula (III)) are dictated by the desired arylsulphonamide hydroxamate final product or an alpha halo acid of formula (XI)

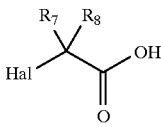

(XI)

wherein $R_7$ and $R_8$ are dictated by the desired arylsulphonamide hydroxamate final product and Hal is a halogen such as bromo. This first building block (protected alpha amino acid or alpha halo acid) is coupled to the groups A carried by solid phase reaction component of the invention, for example one of the preferred solid phase reaction components of the invention carrying a plurality of groups of formula (IV) or (IVA). In the latter case, the coupling of the protected alpha-amino acid or alpha-halo acid carboxyl group to the nitrogen of the group A carried by the solid phase reaction component of the invention may be facilitated by the use of a coupling agent such as is commonly used in peptide synthesis, for example a carbodiimide (e.g. diisopropylcarbodiimide), a phosphonium salt (e.g. benzotriazol-1-yl-oxy-tris-(dimethylamino)phosphonium hexafluorophosphate) or a uronium salt (e.g. 2-(1H-benzotriazol-1-yl)-1,1,3,3-tetramethyluronium hexafluorophosphate), with the optional addition of an additive such as 1-hydroxybenzotriazole. Alternatively this first building block may be coupled to the group A carried by the solid phase reaction component of the invention as an activated ester, for example a pentafluorophenyl ester, in the presence of dimethylaminopyridine.

In the case where the first building block is a protected alpha-amino acid the N-protecting group (eg Fmoc or Aloc) may be removed by treatment of the reaction product with a basic amine such as piperidine in the case of base labile protecting groups (e.g. Fmoc) or treatment with a suitable palladium catalyst in the case of palladium labile protecting groups (e.g. Aloc). The free amino group then serves as the site for formation of the appropriate arylsulphonamide and alkylation of the sulphonamide nitrogen to complete the synthesis of the desired arylsulphonamide hydroxamate, which can then be cleaved from the solid substrate, eg by acid hydrolysis of the bond designated (a).

In the case where the first building block is an alpha-halo acid the halogen may be displaced by reaction with an amine to form a secondary amine which serves as the site for formation of the sulphonamide to complete the synthesis of the desired arylsulphonamide hydroxamate, which can then be cleaved from the solid substrate, eg by acid hydrolysis of the bond designated (a).

Examples 1–5 disclose the preparation of solid phase reaction components of the invention and Examples A–H illustrate their utility in the preparation of biologically active hydroxamic acid derivatives.

The amino acids used in the examples below were commercially available or were prepared according to literature procedures.

The following abbreviations have been used throughout:

| | |
|---|---|
| BPB | Bromophenol blue |
| DMF | N,N-Dimethylformamide |
| DMSO | Dimethylsulfoxide |
| Fmoc | 9-Fluorenylmethoxycarbonyl |
| pyBOP | Benzotriazol-1-yl-oxy-tris-pyrrolidino-phosphonium hexafluorophosphate |
| HOBt | N-Hydroxybenzotriazole |
| THF | Tetrahydrofuran |
| TFA | Trifluoroacetic acid |
| TLC | Thin layer chromatography |
| TBTU | 2-(1H-Benzotriazol-1-yl)-1,1,3,3-tetramethyluronium tetrafluoroborate |
| Pmc | 2,2,5,7,8-Pentamethylchroman-6-sulfonyl |
| Z | Benzyloxycarbonyl |

$^1$H and $^{13}$C NMR spectra were recorded using either a Bruker AC 250E spectrometer at 250.1 and 62.9 MHz respectively, or on a Bruker AMX500 at 500.13 and 125.7 MHz respectively. Elemental microanalyses were performed by Medac Ltd (Department of Chemistry, Brunel University, Uxbridge, Middlesex UB8 3PH).

EXAMPLE 1

4-(O-Methylhydroxylamine)phenoxymethyl-copoly (styrene-1% divinylbenzene)-resin (100–200 mesh)

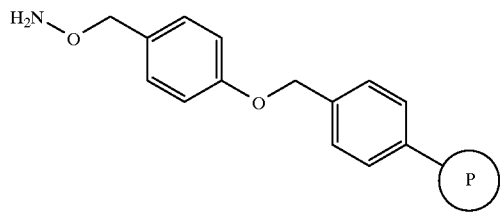

4-(Hydroxymethyl)phenoxymethyl-copoly(styrene 1% divinylbenzene)-resin (100–200 mesh) ("Wang" resin) (1.83 g, 0.7 mmol/g loading, 1.28 mmol) was suspended in dry THF (20 cm$^3$) and gently agitated for 30 minutes under a blanket of argon. N-Hydroxyphthalimide (624 mg, 3.82 mmol) and triphenylphosphine (1.005 g, 3.82 mmol) were added and the mixture was agitated until these reagents dissolved. Diethylazodicarboxylate (721 mg, 3.28 mmol) was added by cannula to give a bright red solution and the mixture was shaken. Most of the colour dissipated from the reaction mixture after 45 minutes. After 18 h the resin was collected by filtration, washed successively with THF, DMF, dichloromethane, methanol and finally thoroughly with dichloromethane and then dried in vacuo; $\nu_{max}$ (KBr) 1726 (vs), 1687, 1593 cm$^{-1}$ The resin from above was suspended in DMF (10 cm$^3$) and hydrazine (~100%) (1.5 cm$^3$) was added. The pale yellow solution was heated at 50° C. for 2 h and then gently agitated overnight. The desired resin (4-(O-methylhydroxylamine) phenoxymethyl-copoly(styrene-1% divinylbenzene)-resin (100–200 mesh)) was filtered, and washed with DMF (2×15 cm$^3$), CH$_2$Cl$_2$ (2×15 cm$^3$), methanol (20 cm$^3$) and finally with CH$_2$Cl$_2$ (3×15 cm$^3$) and then dried. Ir (KBr) showed the absence of any carbonyl containing substituent confirming hydrazinolysis of the phthalimide. Elemental analysis of the resin confirmed the presence of nitrogen and suggested a loading of 0.68 mmol/g: C 89.17, H 7.70, N 0.95%. [Note: The loading obtained varied for different batches of the resin due to variability in the loading of the starting Wang resin, but in each case elemental analysis suggested that quantative conversion was achieved.]

EXAMPLE 2

O-Hydroxylamine-2'-chlorotrityl-copoly(styrene-1%-divinylbenzene)-resin (200–400 mesh)

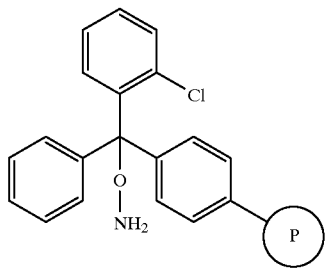

Chloro-2'chlorotrityl-copoly(styrene-1%-divinylbenzene) resin (200–400 mesh) (0.5 g, 1.5 mmol/g, 0.75 mmol) was allowed to swell in dry DMF (3 cm$^3$) for 10 minutes. Diisopropylamine (0.398 cm$^3$, 2.28 mmol) was added to a solution of N-hydroxyphthalimide (0.367g, 2.25 mmol) in DMF (3 cm$^3$) and the subsequent bright red solution added in one portion to the resin suspension and the resulting mixture was then gently agitated for 4 hr under an argon atmosphere. The resin was collected by filtration and washed thoroughly with DMF (3×10 cm$^3$), dichloromethane (2×10 cm$^3$), followed by methanol (3×10 cm$^3$, 3 cycles), dichloromethane (2×10 cm$_3$) and dried. The pale yellow resin had $\nu_{max}$ (KBr) 1737(vs) cm$^{-1}$.

THF (5 cm$^3$) was added to the resin which was allowed to swell for 15 minutes. Hydrazine hydrate (4 cm$^3$) was added to the mixture and the resulting mixture was gently agitated for 3 hr. Following filtration and washing as above the resin was dried. It exhibited no stretch at 1737 cm$^{-1}$ in the i.r spectrum and was stained blue by a 2% solution of bromophenol blue (BPB) in DMF.

EXAMPLE 3

4-[4-(O-Methylhydroxylamine)-3-methoxyphenoxy]-(N-4-methylbenzhydryl)-butyramide-copoly(styrene-1%-divinylbenzene)-resin (100–200 mesh)

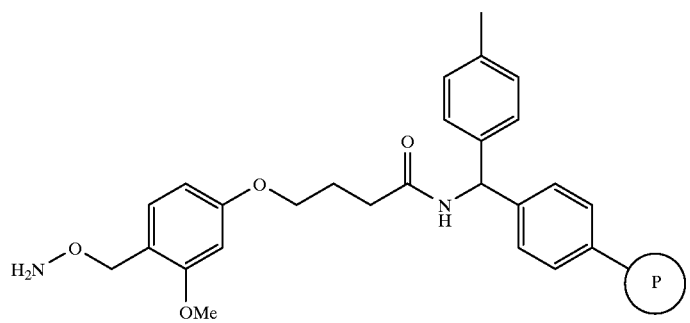

Following the analogous procedure to that described in Example 1, 4-[4-hydroxymethyl-3-methoxyphenoxy]-(N-4-methylbenzhydryl)butyramide-copoly (styrene-1%-divinylbenzene)-resin (100–200 mesh) (0.87 mmol/g loading) was treated with 3 equivalents of triphenylphosphine, N-hydroxyphthalimide and diethylazodicarboxylate in THF to give the N-hydroxyphthalimido derivatised resin which on treatment with hydrazine hydrate gave the desired 4-[4-(O-methylhydroxlamine)-3-methoxyphenoxy]-(N-4-methylbenzhydryl)-butyramide-copoly(styrene-1%-divinylbenzene)-resin.

EXAMPLE 4

4-(2',4'-Dimethoxyphenyl-O-methylhydroxylamine)-phenoxymethyl-copoly(styrene-1%-divinylbenzene)-resin (100–200 mesh)

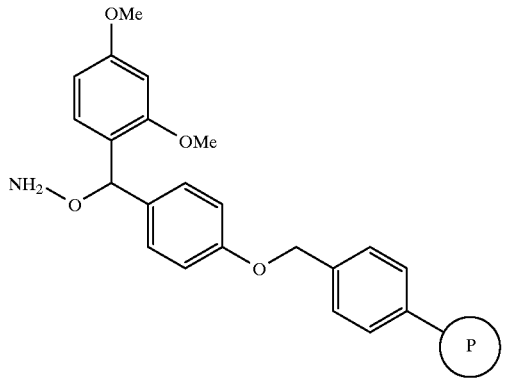

Following the analogous procedure to that described in Example 1, 4-(2',4'-dimethoxyphenyl-O-methylhydroxy)-phenoxymethyl-copoly(styrene-1% divinylbenzene)-resin (100–200 mesh) (0.54 mmol/g loading) was treated with 3 equivalents of triphenylphosphine, N-hydroxyphthalimide and diethylazodicarboxylate in THF to give the N-hydroxyphthalimido derivatised resin which on treatment with hydrazine hydrate gave the desired 4-(2',4'-dimethoxyphenyl-O-methylhydroxylamine)-phenoxymethyl-copoly(styrene-1%-divinylbenzene)-resin.

EXAMPLE 5

4-[4-(1-Aminooxyethyl)-2-methoxy-5-nitrophenoxy]-(N-4-methylbenzhydryl)-butyramide-copoly(styrene-1%-divinylbenzene)-resin (100–200 mesh)

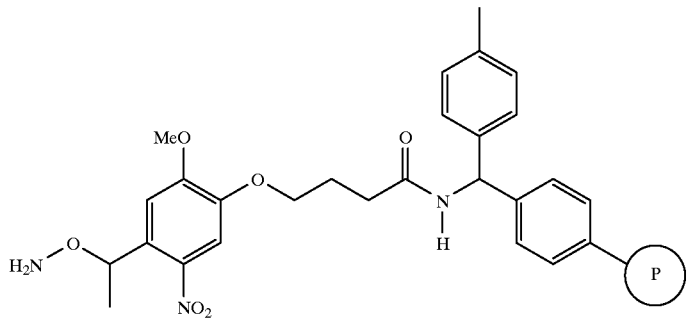

Methyl 4-(4-acetyl-2-methoxyphenoxy)butyrate (10 g) was added to cold 70% nitric acid (140 cm$^3$) and the resulting orange solution was stirred for 2 h and then poured into a beaker containing ice-water (1 dm$^3$). The slurry warmed with stirring overnight to give a yellow solid which was collected and recrystallised from methanol to give methyl 4-(4-acetyl-2-methoxy-5-nitrophenoxy)butyrate as a pale yellow solid (8.5 g). $^1$H NMR (CDCl$_3$) δ2.21 (2H, m, J=6.6 Hz, CCH$_2$C), 2.50 (3H, s, MeCO), 2.57 (2H, t, J=7.1 Hz, CH$_2$CO), 3.7 (3H, s, OMe), 3.99 (3H, s, OMe), 4.16 (2H, t, J=6.2 Hz, CH$_2$O), 6.75 (1H, s, aromatic) and 7.62 (1H, s, aromatic).

Methyl 4-(4-acetyl-2-methoxy-5-nitrophenoxy)butyrate (5.06 g) in methanol (300 cm$^3$) was cooled with stirring at 0° C. under argon. Sodium borohydride (640 mg) was added portionwise and the resulting solution stirred at 40° C. overnight. Further sodium borohydride (500 mg) was added as TLC analysis indicated that starting material remained. After a further 3 h TLC analysis indicated that the reaction was complete. The reaction was cooled, acidified with dilute (1M) hydrochloric acid and evaporated to dryness. The residue was dissolved in ethyl acetate (250 cm$^3$) washed with dilute aqueous acid and brine, dried over magnesium sulphate and filtered. The solvent was evaporated to leave a yellow oil which solidified on standing. After recrystallisation from methanol/diethyl ether, methyl 4-[4-(1-hydroxyethyl)-2-methoxy-5-nitrophenoxy]butyrate was obtained as yellow needles (5.04 g, ~100%). $^1$H NMR (CDCl$_3$) δ1.52 (3H, d, J=8.3 Hz, MeCHO), 2.18 (2H, m, CCH$_2$C), 2.53 (2H, t, J=6.5 Hz, CH$_2$CO), 3.71 (3H, s, OMe), 3.95 (3H, s, OMe), 4.13 (2H, t, J=7.3 Hz, CH$_2$O), 5.52 (1H, q, J=8.2 Hz, CHOH), 7.29 (1H, s, aromatic) and 7.57 (1H, s, aromatic).

Methyl 4-[4-(1-hydroxyethyl)-2-methoxy-5-nitrophenoxy]butyrate (5.04 g) from above was stirred with lithium hydroxide monohydrate in methanol using conventional protocols. 4-[4-(1-Hydroxyethyl)-2-methoxy-5-nitrophenoxy]butyric acid was obtained as an amorphous yellow solid (4.0 g, 83%). $^1$H NMR (CDCl$_3$) δ1.34 (3H, d, J=11 Hz, MeCOH), 2.03 (2H, m, CCH$_2$C), 2.38 (2H, t, J=7.3 Hz, CH$_2$CO), 3.81 (3H, s, OMe), 3.96 (2H, t, J=7.4 Hz, CH$_2$O), 4.13 (2H, brs, OH), 5.38 (1H, q, J=10.8 Hz, CHOH), 7.19 (1H, s, aromatic, and 7.43 (1H, s, aromatic).

4-Methylbenzhydrylamine-copoly(styrene-1%-divinylbenzene)-resin (100–200 mesh) (2.0 g, 0.7 mmol/g loading, 1.4 mmol) was placed in DMF (10 cm$^3$). 4-[4-(1-Hydroxyethyl)-2-methoxy-5-nitrophenoxy]butyric acid (1.51 g, 4.8 mmol), HOBt (734 mg, 4.8 mmol) and TBTU (1.54 g, 4.8 mmol) were added and the mixture agitated. N-Methylmorpholine (0.88 cm$^3$, 8 mmol) was added and the resulting mixture was gently agitated for 18 h in a flask protected from the light by aluminium foil. The bright yellow resin (2.45 g) was collected by filtration, thoroughly washed as described in Example 1 and dried in vacuo. The Kaiser test was negative which contrasted with that of the unsubstituted resin. $v_{max}$ (KBr) 1672 (s) cm$^{-1}$.

The above resin (2.41 g) was placed in a small conical flask under argon and THF (25 cm$^3$) was added. The resin was allowed to swell for 20 minutes and triphenylphosphine (1.67 g, 6.36 mmol) and N-hydroxyphthalimide (1.038 g, 6.36 mmol) were added. The mixture was shaken together in the dark to dissolve the reagents and then cooled to 0°. Diethylazodicarboxylate (1.0 cm$^3$, 6.36 mmol) was added and the solution turned red. After shaking the reaction at room temperature for 48 h the resin was then collected by vacuum filtration, washed as described in Example 1 and dried in vacuo. $v_{max}$ (KBr) 1792, 1734 (vs) and 1669 (s) cm$^{-1}$.

Hydrazine (2.2 cm$^3$) was added to a suspension of this resin (2.7 g) in DMF (15 cm$^3$) under argon. The mixture was shaken at room temperature in the dark overnight and the resin (4-[4-(1-aminooxyethyl)-2-methoxy-5-nitrophenoxy]-(N-4-methylbenzhydryl)-butyramide-copoly(styrene-1%-divinylbenzene)-resin (100–200 mesh)) was then collected, washed and dried as described in Example 1. It showed no phthalimide carbonyl stretch in the IR spectrum. $v_{max}$ (KBr) 1673 (s) cm$^{-1}$.

Example A

Use of the resin from Example 1 in the preparation of a peptide hydroxamate derivative: Benzyloxycarbonyl-L-prolyl-L-leucyl-L-alanylhydroxamic acid

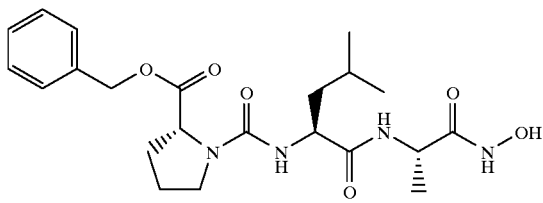

The resin (4-(O-methylhydroxylamine)phenoxymethyl-copoly(styrene-1% divinylbenzene)-resin (100–200 mesh)) as prepared in Example 1 (200 mg, 0.14 mmol) was suspended in DMF (6 cm$^3$). Fmoc-Alanine (217 mg, 0.7 mmol), HOBt (107 mg, 0.7 mmol), pyBOP (364 mg. 0.7 mmol) and N-methyl morpholine (0.123 cm$^3$, 1.12 mmol) were added and the suspension was agitated for 4 h. The resin was filtered, washed with DMF and then suspended and agitated in a 20% solution of piperidine in DMF for 40 minutes. The solution was drained from the resin which was washed with DMF, dichloromethane, methanol, dichloromethane and finally resuspended in DMF (6 cm$^3$). Following the same protocols described above Fmoc-leucine and benzyloxycarbonylproline were then successively coupled to the resin.

On completion the resin was washed thoroughly and dried in vacuo overnight. The resin was treated with 95% aqueous TFA (10 cm$^3$) for 75 minutes. The TFA solution was collected by filtration, the resin washed with more TFA (~2 cm$^3$) and the combined filtrates evaporated to leave a gum which was triturated with ether to give a white solid. TLC of the white solid indicated a single compound which gave a positive ferric chloride test indicative of a hydroxamic acid. The solid was collected and dried to give the desired benzoxycarbonyl-L-prolyl-L-leucyl-L-alanyl-hydroxamic acid (54 mg, ~90%); $^1$H NMR (CDCl$_3$) δ7.35 (5H, m, aromatic), 5.15 (1H, J=7 Hz, CH$_a$H$_b$O), 5.13 (1H, d, J=7 Hz, CH$_a$H$_b$O), 4.48 (1H, m), 4.33 (1H, m), 4.23 (1H, m) 3.52 (2H, m, pro), 1.9–2.2 (3H, m), 1.48–1.78 (2H, m), 1.48 (3H, d, J=8.2 Hz, ala), 1.25 (2H, m, CH$_2$ leu), 0.86 (6H, m, CH$_3$-leu); $^{13}$C NMR (CDCl$_3$) δ173.5, 172.2, 169.3, 156.4, 136.0, 128.6, 128.4, 127.9, 67.8, 61.5, 53.2, 47.4, 47.3, 39.7, 29.6, 25.1, 24.7, 22.6, 21.4, 17.0.

Example B

Use of the resin from Example 1 in the preparation of a library of 'left hand side' inhibitors of matrix metalloproteinases

Z—AA$_3$—AA$_2$—AA$_1$—NHOH 1 g of the resin (4-(O-methylhydroxylamine) phenoxymethyl-copoly(styrene-1% divinylbenzene)-resin (100–200 mesh)) of Example 1 was placed in each of 10 sealable polypropylene tubes (BioRad) and swelled in DMF (1 cm$^3$). 2.5 mmol (4 equivalents) of one of the Fmoc-amino acids, alanine, D-alanine, phenylalanine, isoleucine, leucine, D-leucine, norleucine, methionine, valine, norvaline, was placed in a tube followed by HOBt (3.85 cm$^3$ of a 0.65 M solution in DMF). Diisopropylcarbodiimide (0.4 cm$^3$) was added to each tube which were then sealed and gently agitated for 18 h when they were drained of solvent and washed thoroughly with DMF. A solution of 30% piperidine in DMF (6 cm$^3$) was added to each tube, the resin was mixed by shaking and then allowed to stand in the solution for 40 minutes, the solvent was drained and the resin washed successively with DMF, methanol and dichloromethane as described above in Example 1 and dried.

The resin from each individual tube was then portioned into 10 tubes (~100 mg/tube) and a 1% solution of bromophenol blue in DMF (1 cm$^3$) added to swell and stain the resin.

0.25 mmol of one of the Fmoc-amino acids alanine, D-alanine, arginine (N$^G$-Pmc), aspartic acid-b-tert-butyl ester, leucine, proline, norleucine, glutamine-y-trityl, thioproline, ε-Boc-lysine was added to one of the tubes derived from the sub-division of the resin from the original ten tubes. HOBt (0.38 cm$^3$ of a 0.65 M solution in DMF) was added to every tube followed by diisopropylcarbodiimide (39 mm$^3$). The tubes were then sealed and agitated overnight. At this time the colour had discharged from almost every tube. A further 0.05 mmol portion each of the Fmoc-amino acid and diisopropylcarbodiimide was added to those tubes which still showed a blue-green colouring; this was discharged within 30 minutes of the addition of the extra reagent. The resin from these tubes was then pooled back into the tube from where it had originated, washed with DMF and then treated with 30% piperidine in DMF for 40 minutes and washed thoroughly as above.

The resin from each of these ten tubes was then redivided into 5 tubes (~200 mg/tube) and allowed to swell in a 1% solution of bromophenol blue in DMF (1 cm$^3$). 5 mmol of one of the Z-amino acids, alanine, phenylalanine, proline, leucine, aspartic acid-δ-tert-butyl ester, was added to one tube from each sub-division followed by HOBt (5 cm$^3$ of a 1.0 M solution in DMF) and by diisopropylcarbodiimide (0.78 cm$^3$). The tubes were gently agitated for 5 h by when the blue colour had been discharged in all tubes. The resin was then repooled into the original tubes as above and thoroughly washed with DMF, dichloromethane and methanol as described previously. The resin, maintained in the 10 tubes, was then dried in vacuo overnight.

5 cm$^3$ of a solution of 5% phenol, 5% water, 2% triisopropylsilane in TFA was added to the resin in each tube and periodically shaken over 60 minutes. The TFA solution was collected by filtration and the resin washed with a further 2 cm$^3$ of TFA. The washings and filtrate from each individual tube were combined and the solvent evaporated to leave a residue which was triturated with cold diisopropylether/hexane to give white solid precipitates. After removal of most of the organic solvent by decanting the precipitates were then lyophilised from 50% aqueous acetontrile to give to give the desired 10 mixtures of 50 tripeptide hydroxamic acids.

Each of the ten mixtures of peptidyl hydroxamic acids was assayed for activity as inhibitors of metalloproteinase enzymes. Those pools showing the greatest inhibitory activity were then subjected to an iterative deconvolution procedure to identify individual active inhibitors.

Example C

Use of the resin from Example 1 in the preparation of a sulfonamide hydroxamate derivative: 2-(N-Decyl-2-acetamido-4-methylthiazol-5-ylsulfonamido)-acetohydroxamic acid

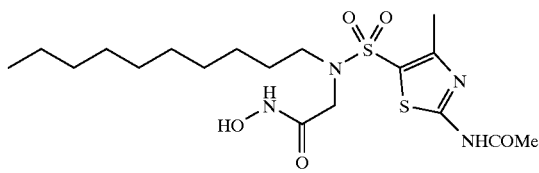

Bromoacetic acid (167 mg, 1.2 mmol) and diisopropylcarbodiimide (94 mm$^3$, 0.6 mmol) were added to a suspension of the resin (4-(O-methylhydroxylamine) phenoxymethyl-copoly(styrene-1% divinylbenzene)-resin (100–200 mesh)) prepared according to Example 1 (250 mg, 0.1 mmol) in DMF (6 cm$^3$). The mixture was agitated for 90 minutes and then the solution was drained from the resin which was washed and dried as described above in Example 1. The resin was soaked in DMSO (2 cm$^3$) and a solution of n-decylamine in DMSO (5 cm$^3$ of a 2M solution, 10 mmol) was added and the mixture shaken for 4 h before the resin was drained and washed thoroughly as before. The resin was then suspended in DMF and 2-acetamido4-methyl-5-thiazolesulfonylchloride (102 mg, 0.4 mmol) was added. The mixture was heated at 60° for 8 h and then the resin was drained, washed and dried as described previously. Cleavage from the resin as in Example A gave a white solid which was purified by column chromatography (10% methanol-dichloromethane; silica) to give the desired 2-(N-decyl-2-acetamido4-methylthiazol-5-ylsulfonamido)-acetohydroxamic acid (23 mg, 51%) as a white solid; $^1$H NMR (CDCl$_3$) $\delta$3.83 (2H, m), 3.05 (2H, m), 2.52 (3H, s, Me), 2.35 (3H, s, NHCOMe), 1.69 (2H, m), 1.15–1.25 (14H, m, alkyl), 0.87 (3H, t, J=7.2 Hz, CH$_3$-alkyl).

Example D

Use of the resin from Example 1 in the preparation of an array of sulfonamide hydroxamate inhibitors of matrix metalloproteinases

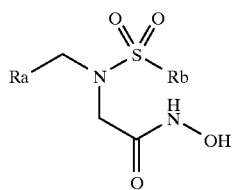

Sulfonamide hydroxamic acid derivatives were prepared as a combinatorial array of individual compounds in purity sufficient for fast throughput assays. The resin (4-(O-methyhydroxylamine)phenoxymethyl-copoly(styrene-1% divinylbenzene)-resin (100–200 mesh)) was loaded with bromoacetic acid as described in Example C. Elemental analysis of this different batch of resin confirmed that coupling had taken place: C 83.34, H 7.04, N 0.86, Br 5.40% and suggested a loading of 0.65 mmol. 1 g of this resin was placed in each of 36 plastic Econopac tubes (BioRad) and swelled in DMF (5 cm$^3$). The excess DMF was drained off and the tubes grouped into nine groups of four tubes. A solution (5 cm$^3$ of a 2M solution in either DMF or DMSO) of one of the amines, benzylamine, 4-methylbenzylamine, 4-methoxybenzylamine, 4-fluorobenzyiamine, 4-chlorobenzylamine, pyridin-3-ylmethylamine, thien-2-ylmethylamine, furan-2-ylmethylamine and 3,4-dioxymethylenebenzylamine was each added to each of four tubes (within one of the nine groups) which were then sealed and mixed thoroughly for 2 h. The solvent was removed, the resin washed as in Example C and reswelled in DMF. The tubes were regrouped into four groups each of nine tubes. Following a protocol analogous to that used in Example C, a DMF solution of 10 equivalents of one of the sulfonyl chlorides, 3-chloropropylsulfonyl chloride, hexylsulfonyl chloride, octylsulfonyl chloride and decylsulfonyl chloride was added to each of the nine tubes (within one of the four groups) so that all 36 combinations of sulfonamides were prepared. After removal of the sovent by filtration, thorough washing with DMF, methanol and dichloromethane as above, and drying under vacuum for several hours the products were cleaved from the resin as in Example C directly into plastic centrifuge tubes. The TFA was removed by centrifugal evaporation and the resulting hydroxamic acids lyophilised from aqueous acetonitrile. All samples gave positive ferric chloride spots on TLC analysis {10% methanol in DCM/silica} (Table). All 36 samples were submitted for assay as inhibitors of metalloproteinases from which active compounds were identified.

TABLE

TLC {10% methanol in DCM/silica} $R_f$ values for the compounds of Example D

| Ra | Rb | | | |
|---|---|---|---|---|
| | —(CH$_2$)$_3$Cl | —C$_6$H$_{13}$ | —C$_8$H$_{17}$ | —C$_{10}$H$_{21}$ |
| C$_6$H$_5$— | 0.25 | 0.2 | 0.45 | 0.45 |
| 4-MeC$_6$H$_4$— | 0.35 | 0.4 | 0.4 | 0.4 |
| 4-MeOC$_6$H$_4$— | 0.5 | 0.35 | 0.5 | 0.4 |
| 4-FC$_6$H$_4$— | 0.3 | 0.3 | 0.5 | 0.5 |
| 4-ClC$_6$H$_4$— | 0.15 | 0.2 | 0.4 | 0.4 |
| pyridin-3-yl | 0.0 | 0.05 | 0.0 | 0.05 |
| thien-2-yl | 0.1 | 0.35 | 0.65 | 0.6 |
| furan-2-yl | 0.15 | 0.3 | 0.3 | 0.4 |
| 3,4-(CH$_2$)O$_2$C$_6$H$_3$— | 0.3 | 0.4 | 0.5 | 0.45 |

Example E

Use of the resin from Example 2 in the preparation of a peptide hydroxamate derivative: Benzyloxycarbonyl-L-phenylalanyl-L-alanylhydroxamic acid

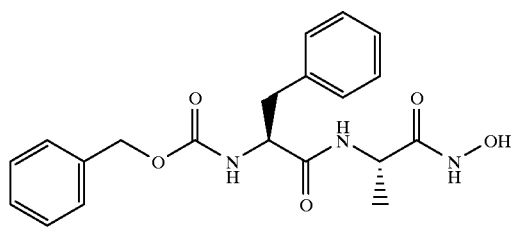

FMOC-Alanine (187 mg, 0.6 mmol), HOBt (92 mg, 0.6 mmol) and TBTU (194 mg, 0.6 mmol) were dissolved together in DMF (5 cm$^3$). Diisopropylethylamine (0.183 cm³, 1.05 mmol) was added and the resulting solution added to pre-swelled (in DMF) modified resin from Example 2 (O-hydroxylamine-2'-chlorotrityl-copoly (styrene-1%-divinylbenzene)-resin (200–400 mesh)) (100 mg, 0.15 mmol) and the mixture was then shaken gently together for 12 h. The resulting resin was then filtered, washed thoroughly with DMF and treated with 20% piperidine in DMF (7 cm³) for 30 minutes. After removal of the solvent and thorough washing as described in Example 1 the resin was resuspended in DMF (1 cm³). A solution of Z-phenylalanine (180 mg, 0.6 mmol), HOBt (92 mg, 0.6 mmol) and diisopropylcarbodiimide (94 mm³, 0.6 mmol) in DMF (5 cm³) was added and the resin suspension was gently agitated overnight by which time the initially blue staining of BPB had been discharged. The resin was then drained and washed as described in Example 1 and dried in vacuo. It had $v_{max}$ (KBr) 1668 (s) cm⁻¹.

The resin from above was suspended in a 20% solution of TFA in dichloromethane, containing 1% (v/v) of triethylsilane, under argon (5 cm³) for 45 minutes. The solution was removed from the resin by filtration, the resin washed with a further portion (1 cm³) of the cleavage mixture, the filtrate and washings combined and evaporated to leave benzyloxycarbonyl-L-phenylalanyl-L-alanylhydroxamic acid as a white solid. TLC analysis indicated a single compound, $R_f$ 0.45 (10% methanol in dichloromethane) which gave a positive ferric chloride test. ¹H NMR (CDCl₃) δ1.36 (3H, d, J=9 Hz, Me alanine), 3.12 (2H, m, CH₂Ph), 4.14 (1H, m, CH), 4.4 (1H, m, CH), 5.13 (2H, brs, OCH₂Ph), 7.71–7.33 (~1 OH, m, aromatic) 7.8 (1H, d, NH).

Example F

Use of the resin from Example 3 in the preparation of a sulfonamide hydroxamate derivative: 2-(N-Benzyl-benzylsulfonamido)-acetohydroxamic acid

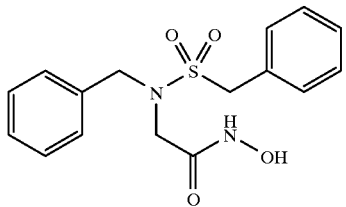

The resin of Example 3 (4-[4-(O-methylhydroxylamine)-3-methoxyphenoxy]-(N-4-methylbenzhydryl)butyramide-copoly(styrene-1%-divinylbenzene)-resin (100–200 mesh)) (0.5 g) was suspended in DMF (3 cm³). Diisopropylcarbodiimide (0.3 cm³) was added to a solution of bromoacetic acid (670 mg) in DMF (3 cm³) and after 3 minutes the resulting solution was added to the resin suspension and gently mixed together for 2 h. The resin was collected by filtration and washed thoroughly with DMF, methanol, methanol-dichloromethane, dichloromethane and ether. It was then dried in vacuo at 45° C. for 18 h. Elemental analysis of the resin suggested a loading of 0.66 mmol/g: C; 79.11; H, 6.78; N, 2.08; Br, 5.25%.

The resin from above swelled in DMF (3 ml) was treated with (0.33 cm³, 3 mmol) benzylamine and gently agitated at room temperature overnight. The solvent was removed by filtration and the resin washed as described above in Example 1 and dried. The resin was swelled in DMF (3 ml), and phenylmethylsulfonyl chloride (0.8 g, 4 mmol) was added and the mixture was gently agitated for 2 h at room temperature. The resin was filtered and washed as described above in Example 1 and dried. A solution of 1% TFA in DCM (3 ml) was added to the resin at room temperature and the mixture gently agitated for 1 h. The resin was filtered and washed with DCM, methanol and DCM, the filtrates combined and evaporated under reduced pressure to give crude 2-(N-benzyl-benzylsulfonamido)-acetohydroxamic acid (0.39 g): TLC ferric chloride positive spot $R_f$ 0.15 {10% methanol in DCM/silica}.

Example G

Use of the resin from Example 4 in the preparation of a sulfonamide hydroxamate derivative: 2-(N-Benzyl-benzylsulfonamido)-acetohydroxamic acid This resin of Example 4 (4-(2',4'-dimethoxyphenyl-O-methylhydroxylamine)-phenoxymethyl-copoly (styrene-1%-divinylbenzene)-resin (100–200 mesh)) (0.25 g) was suspended in DMF (3 cm³). Diisopropylcarbodiimide (0.24 cm³) was added to a solution of bromoacetic acid (420 mg) in DMF (3 cm³) and after 3 minutes the resulting solution was added to the resin suspension and gently mixed together for 2 h. The resin was collected by filtration and washed thoroughly with DMF, methanol, methanol-dichloromethane, dichloromethane and ether. It was then dried in vacuo at 45° C. for 18 h. Elemental analysis of the resin suggested a loading of 0.58 mmol/g: C; 84.31; H, 7.28; N, 0.82; Br, 4.65%.

Following the procedure of Example F the above resin was treated in turn with benzylamine and phenylmethylsulfonyl chloride. A solution of 10% acetic acid in DCM (3 ml) was added to the resin at room temperature and the mixture gently agitated for 2 h. The resin was filtered and washed with DCM, methanol and DCM, the filtrates combined and evaporated under reduced pressure to give crude 2-(N-benzyl-benzylsulfonamido)-acetohydroxamic acid (0.22 g).

Example H

Use of the resin from Example 5 in the preparation of a peptide hydroxamate derivative: Benzyloxycarbonyl-L-prolyl-L-leucyl-L-alanylhydroxamic acid Using procedures analogous to those described in Example A, the tripeptide Z-L-prolyl-L-leucyl-L-alanyl was synthesised attached to the resin of Example 5 (4-[4-(1-aminooxyethyl)-2-methoxy-5-nitrophenoxy]-(N4-methylbenzhydryl)-butyramide-copoly (styrene-1%-divinylbenzene)-resin (100–200 mesh)). Following drying, the elaborated resin (50 mg) in acetonitrile (1.5 cm³) was blanketed with argon in a stoppered reaction vial. The vial was placed 5 cm away from a 365 nm light source and irradiated for 15 h. TLC of the resulting solution indicated a ferric chloride positive component with RF equivalent to that of the tripepetide hydroxamic acid of Example A. HPLC of the solution identified the desired tripeptide as the major product of the reaction along with an unidentified non-hydroxamic acid component.

We claim:

1. A solid phase reaction product comprising a solid substrate that is substantially insoluble in aqueous or organic reaction media, wherein the solid substrate comprises a base substrate carrying a plurality of covalently bound hydroxylamine or protected hydroxylamine groups of formula (A):

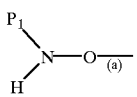

wherein $P_1$ is hydrogen or an amino protecting group and the bond designated (a) is one which (i) is cleavable under acid conditions or by photolysis and (ii) covalently links the group (A) to the base substrate via a linker group of formula (D):

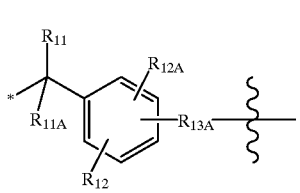

wherein the base substrate is directly linked to the linker group of formula (D) via $R_{13A}$, and the hydroxylamine group of formula (A) is directly linked to the linker group of formula (D) at *, wherein in formula (D):

$R_{11}$ and $R_{11A}$ independently represent hydrogen, $C_1$–$C_6$ alkyl, or phenyl optionally substituted by one or more substituents selected from $C_1$–$C_6$ alkyl, $C_1$–$C_6$ alkoxy, halogen, nitrile or $NO_2$;

$R_{12}$ and $R_{12A}$ independently represent hydrogen, $C_1$–$C_6$ alkyl, $C_1$–$C_6$ alkoxy, halogen, nitrile or $NO_2$;

$R_{13A}$ represents a bond or a group —$(X^1)_q$—Y—, wherein q is 0 or 1; $X^1$ represents —C(=O)—, —CH$_2$—, —CH$_2$C(=O)—, —O(CH$_2$)$_n$C(=O)—, —O(CH$_2$)$_n$C(=O)—(A$^1$)$_m$— or —O(CH$_2$)$_n$C(=O)—(A$^1$)$_m$—B$^1$—, wherein n is an integer from 1 to 6; m is 0 or 1; A$^1$ represents —OCH(R$^1$)—NH—, wherein R$^1$ is the side chain of a natural or unnatural alpha amino acid, B$^1$ represents a spacer group —NH(CH$_2$)$_p$—, wherein p is 0 or an integer from 1 to 6; and Y represents —O— or —NH—; provided that when $R_{13A}$ is a bond or —O—, then $R_{11}$, $R_{11A}$, $R_{12}$ and $R_{12A}$ are not each hydrogen.

2. The solid phase reaction product as claimed in claim 1, wherein $P_1$ represents hydrogen.

3. The solid phase reaction product as claimed in claim 1, wherein $P_1$ represents ((phenyl)CH$_2$)— optionally substituted in the phenyl ring by one or more substituents selected from $C_1$–$C_6$ alkyl, $C_{1–C6}$ alkoxy, halogen, nitrile and $NO_2$.

4. The solid phase reaction product as claimed in claim 1, wherein $P_1$ is hydrogen, 4-methoxybenzyl or 2,4dimethoxybenzyl.

5. The solid phase reaction product as claimed in claim 2, wherein $R_{11}$ and $R_{11A}$ are each independently hydrogen, methyl, phenyl, 4-methylphenyl, 4-methoxyphenyl or 2,4-dimethoxyphenyl.

6. The solid phase reaction product as claimed in claim 3, wherein $R_{11}$ and $R_{11A}$ are each independently hydrogen, methyl, phenyl, 4-methylphenyl, 4-methoxyphenyl or 2,4-dimethoxyphenyl.

7. The solid phase reaction product as claimed in claim 2, wherein $R_{12}$ and $R_{12A}$ are each independently hydrogen or methoxy.

8. The solid phase reaction product as claimed in claim 3, wherein $R_{12}$ and $R_{12A}$ are each independently hydrogen or methoxy.

9. The solid phase reaction product as claimed in claim 1, wherein $P_1$ represents hydrogen, 4-methoxybenzyl or 2,4-dimethoxybenzyl; $R_{11}$ and $R_{11A}$ are each independently hydrogen, methyl, phenyl, 4-methylphenyl, 4-methoxyphenyl or 2,4-dimethoxyphenyl; $R_{12}$ and $R_{12A}$ are each independently hydrogen or methoxy; and $R_{13A}$ represents a bond or a group —$(X^1)_q$—Y—, wherein q is 0 or 1; $X^1$ represents —C(=O)—, —CH$_2$—, —CH$_2$C(=O)—, —O(CH$_2$)$_n$C(=O)—, —O(CH$_2$)$_n$C(=O)—(A$^1$)$_m$— or —O(CH$_2$)$_n$C(=O)—(A$^1$)$_m$—B$^1$—, wherein n is an integer from 1 to 6; m is 0 or 1; A$^1$ represents —OCH(R$^1$)—NH—, wherein R$^1$ is the side chain of a natural alpha amino acid; B$^1$ represents a spacer group —NH(CH$_2$)$_p$—, wherein p is 0 or an integer from 1 to 6; and Y represents —O—or —NH—; provided that when $R_{13A}$ is a bond or —O—, then $R_{11}$, $R_{11A}$, $R_{12}$ and $R_{12A}$ are not each hydrogen.

10. The solid phase reaction product as claimed in claim 1, wherein $R_{13A}$ together with the base substrate to which it is attached is oxymethyl-copoly(styrene-1%-divinylbenzene)resin, oxymethyl-copoly(styrene-2%-divinylbenzene)resin, oxyacetomidomethylpolyethyleneglycol-copoly(styrene-1%-divinylbenezene)resin or oxyacetomidomethylpolyethyleneglycol-copoly(styrene-2%-divinylbenzene)resin.

11. The solid phase reaction product as claimed in claim 9, wherein $R_{13A}$ together with the base substrate to which it is attached is oxymethyl-copoly(styrene-1%-divinylbenzene)resin, oxymethyl-copoly(styrene-2%-divinylbenzene)resin, oxyacetomidomethylpolyethyleneglycol-copoly(styrene-1%-divinylbenezene)resin or oxyacetomidomethylpolyethyleneglycol-copoly(styrene-2%-divinylbenzene)resin.

12. The solid phase reaction product as claimed in claim 1, selected from:

4-(O-methylhydroxylamine)phenoxymethyl-copoly (styrene-1%-divinylbenzene)-resin (100–200 mesh), 4(4-(O-methylhydroxylamine)-3-methoxyphenoxy)-(N-methylbenzhydryl)-butyramide-copoly(styrene-1%-divinylbenzene)-resin (100–200 mesh), 4-(2',4'-dimethoxyphenyl-O-methylhydroxylamine)-phenoxymethyl-copoly-(styrene-1%-divinylbenzene)-resin (100–200 mesh), 4-(4-(1-aminooxyethyl)-2-methoxy-5-nitrophenoxy)-(N-4-methylbenzhydryl)-butyramide-copoly(styrene-1%-divinylbenzene)-resin (100–200 mesh), or O-hydroxylamine-2'-chlorotrityl-copoly(styrene-1%-divinylbenzene)-resin (200–400 mesh).

* * * * *